United States Patent [19]

Miller

[11] 4,281,652

[45] Aug. 4, 1981

[54] CONTROL MEMBER FOR ANAESTHESIA APPARATUS

[76] Inventor: Donald M. Miller, Moroka Hospital, Private Bag X9, Thaba'nchu, South Africa

[21] Appl. No.: 69,998

[22] Filed: Aug. 27, 1979

[30] Foreign Application Priority Data

Sep. 7, 1978 [ZA] South Africa .................. 78/5078

[51] Int. Cl.³ .............................................. A61M 16/00
[52] U.S. Cl. ..................... 128/204.25; 128/205.17; 128/205.24; 128/205.25; 128/911
[58] Field of Search ................. 128/203.28, 204.25, 128/205.13, 205.14, 205.15, 205.17, 205.24, 205.25, 911

[56] References Cited

U.S. PATENT DOCUMENTS

| | | | |
|---|---|---|---|
| 2,875,756 | 3/1959 | Gagnan | 128/204.25 |
| 3,814,092 | 6/1974 | Simionescu et al. | 128/203.28 |
| 3,856,051 | 12/1974 | Bain | 128/911 |
| 3,881,480 | 5/1975 | Lafourcade | 128/205.24 X |
| 3,901,230 | 8/1975 | Henkin | 128/205.17 |
| 3,973,564 | 8/1976 | Carden | 128/205.14 |
| 4,007,737 | 2/1977 | Paluch | 128/911 |

Primary Examiner—Henry J. Recla

[57] ABSTRACT

A flow control device for inhalation anaesthesia apparatus, the control device being connectable between a co-axial tube system and a face mask or the like and having a jet whereby exhaled gases are preferentially directed into an inner supply tube of the co-axial system. The control device has a body member in which the jet is removably secured and to which an outer connecting member is connectable. A further inner connecting member is located within the outer connecting member and is secured thereto by vanes. There is a space between the inner connecting member and the body member so that there is fluid communication between the interior of the inner connecting member and the annular space between it and the outer connecting member. The inner tube of the co-axial system is connected to the inner connecting member and the outer tube to the outer connecting member. A rebreathing bag with a control valve is located at the end of the inner tube remote from the control device and a port to which a venting control valve or a ventilating mechanism may be connected is provided at the corresponding end of the outer tube. With the control device of the invention it is possible to change from a Mapleson-'A'-like system to a modified Mapleson-'D' or 'E' system, and vice versa, with ease and safety with significantly lower gas flow rates with spontaneous breathing.

6 Claims, 2 Drawing Figures

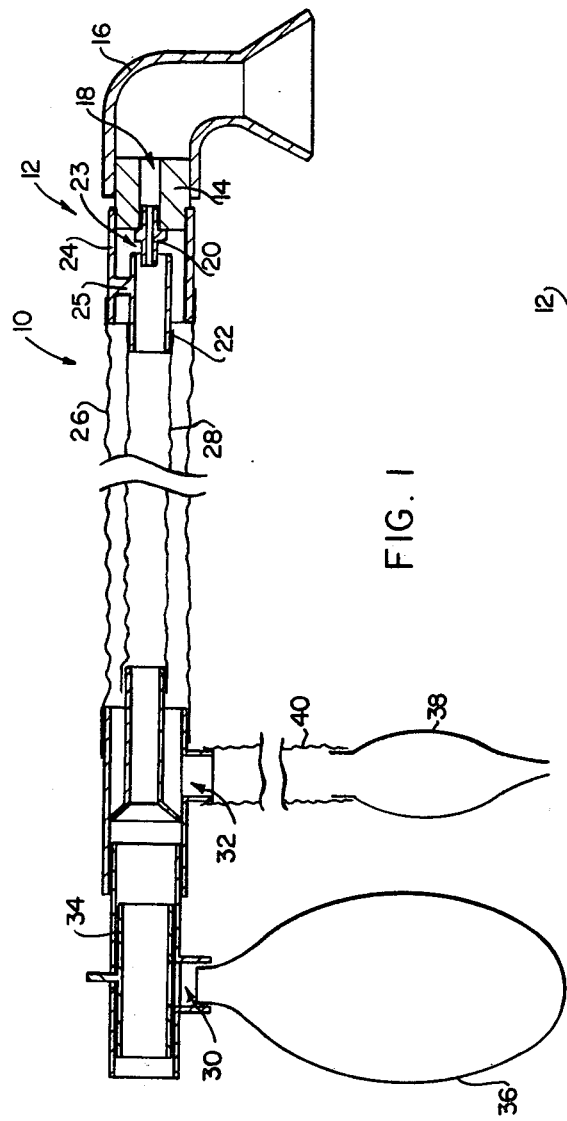
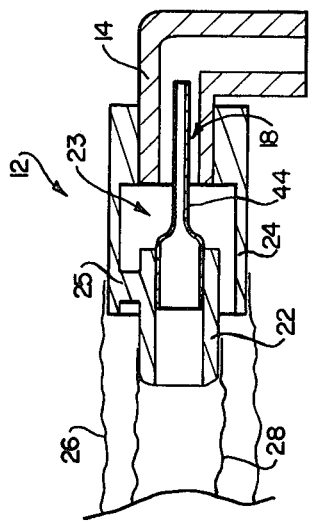

CONTROL MEMBER FOR ANAESTHESIA APPARATUS

SCOPE OF THE INVENTION

THIS INVENTION relates to anaesthesia apparatus, more particularly to a fluid flow control device for inhalation anaesthesia apparatus and to such an apparatus.

STATEMENT OF PRIOR ART

A number of anaesthetic circuits are known, several of which have co-axial tube systems. One of these systems is the modified Mapleson-'D' (or Bain) system as described in Canadian Anaesthetic Society Journal, volume 19 No. 4 July 1972. The efficiency and value of this circuit for controlled ventilation have been amply demonstrated. However, during spontaneous breathing a substantial fresh gas flow is required if re-breathing is to be prevented. It has been shown that carbon dioxide levels can only be maintained by considerable active ventilation when flow rates of 150 ml/kg/min or less are used.

OBJECT OF THE INVENTION

The object of the invention is to provide a coaxial system which incorporates the advantages of the Bain system and which may be used with spontaneous breathing with fresh gas flows considerably less than that required by the Bain system.

BROAD STATEMENT OF THE INVENTION

According to the invention there is provided a fluid flow control device for an inhalation anaesthesia apparatus, which includes a first connecting means for connecting the control device to a patient for supplying him with anaesthetic fluids;

a second connection means for connecting the control device to a supply tube through which anaesthetic fluids may be supplied to the patient;

a third connection means for connecting the control device to an outlet tube through which fluids may be vented to the atmosphere; and a flow directing means for directing fluids exhaled by the patient preferentially into the supply tube.

The flow directing means may direct exhaled fluids preferentially into the supply tube until the pressure in the supply tube reaches a pre-determined value, or until a predetermined volume of fluid has flowed into the supply tube, and thereafter into the outer tube. The flow directing means may also be such that fluids are inhaled preferentially from the supply tube.

The second and the third connection means may comprise a tubular supply member and a tubular outlet member, respectively, to which the supply tube and the outlet tube are respectively connected. There may also be at least one direct communication passage between the supply member and the outlet member. Conveniently, the supply member and the outlet member may be co-axial, the supply memeber being located within the outlet member. The end of the outlet member opposite that to which the outlet tube is connected may extend beyond the corresponding end of the supply member such that the interior of the supply member is in direct fluid communication with the annular space between the supply member and the outlet member.

The flow directing means may conveniently be a jet which projects into the supply member from its exit end, ie the end opposite that to which the supply tube is connected. In a preferred form, the control member may have a body member in which the jet is removably securable.

In order to cater for cases such as with children where it is necessary to minimise dead space, a tubular dead space minimising member may be provided which is engageable with the exit end of the supply member to extend therefrom into the body member with the jet removed.

The control device may form part of a face mask or catheter mount.

The invention extends to an inhalation anaesthesia apparatus which includes a fluid flow control device in accordance with the invention.

The apparatus may have supply and outlet tubes connected to the flow control device. As indicated earlier, these tubes may be co-axial with the supply tube being located within the outlet tube.

At their ends remote from the flow control device the supply and outlet tubes may have ports. A re-breathing bag may be connected to the port of the supply tube. A closure means may be provided for closing this port such that the re-breathing bag may be included in the system or not, as required.

A venting control valve or a ventilating mechanism for controlling ventilation of the patient may be connected to the said port of the outer tube. If required, the ventilating mechanism may be connected to the port by a length of tubing.

In a preferred form the supply and outlet tubes are corrugated and co-axial with the effective annular cross-sectional area between the supply and outlet tubes being less than the effective cross-sectional area of the supply tube.

It will be appreciated by those skilled in the art that anaesthesia apparatus utilising the flow control member may easily, quickly and safely be converted from a Mapleson-'A'-like system to a Mapleson-'D' or 'E' system and vice versa, whether in a co-axial form or not. Further, a circle carbon dioxide absorber can easily be connected between the ports at the ends of the supply and outlet tubes. In addition, it is easy with the apparatus of the invention to change from controlled to spontaneous ventilation.

DESCRIPTION OF PREFERRED EMBODIMENT

The invention is now described, by way of examples, with reference to the accompanying drawings, in which:

FIG. 1 shows schematically portion of an inhalation anaesthesia apparatus that is in accordance with the invention and incorporates a flow control device in accordance with the invention; and FIG. 2 shows schematically the flow control device modified to minimise dead-space.

Referring to FIG. 1, a portion of an inhalation anaesthesia apparatus is designated generally by reference numeral 10. The apparatus 10 includes a fluid flow control device 12. The device 12 comprises a tubular body member 14 which may be straight as shown in FIG. 1, or angled, as shown in FIG. 2. Secured about the body member 14 at one end is a face mask 16. The body member 14 has a bore 18, in which is removably secured a jet 20. As seen in FIG. 1, the jet 20 projects from the body member 14 in the opposite direction to the face mask 16. Instead of the face mask 16 a catheter mount (not shown) may be secured to the body member 14. The body member 14 may form part of the catheter mount.

The fluid flow control device 12 also comprises a supply tube connector 22 and an outlet tube connector 24. The connector 22 is co-axially located within the connector 24, being supported by three vanes, one vane 25 being shown. One end of the outer connector 24 fits over the end of the body member 14 opposite that to which the face mask 16 is secured, and is removably secured thereto in a fluid-tight manner. The corresponding end of the inner connector 22 is suitably spaced from the said end of the outer connector 24 so that there is a space 23 between this end of the inner connector 22 and the body member 14 through which fluids may flow. As shown the jet 20 projects into the inner connector 22.

An outer tube 26, of a co-axial tube system, is connected at one end to the free end of the outer connector 24. An inner tube 28 is connected at its corresponding end to the free end of the inner connector 22. The free end of the inner connector 22 projects beyond that of the outer connector 24 to facilitate attachement of the tubes 28 and 26 thereto.

The ratio of the diameters of the outer tube 26 and the inner tube 28 is an important feature of the invention. The cross-sectional area of the effective annular space between the outer tube 26 and the inner tube 28 should be less than the cross-sectional area of the inner tube 28. For example, when using an inner tube 28 with an internal diameter of 17 mm and an external diameter of 20 mm then the outer tube 26 should have an internal diameter of approximately 26 mm. It may be preferable to use even larger diameter tubes such as an inner tube 28 with an internal diameter of 20 mm and an external diameter of 25 mm and an external tube 26 with an internal diameter of 30 mm. It will be appreciated by those skilled in the art that these tubes 26 and 28 have larger diameters than conventional co-axial systems. It will further be noted that both the inner and outer tubes 28 and 26 are corrugated.

At their ends remote from the connectors 22 and 24 the inner and outer tubes 28 and 26 have ports 30 and 32 respectively. The port 30 is closable by means of a closure member 34 or a suitable plug inserted into the port 30. In the particular embodiment shown, a rebreathing bag 36 is shown connected to the port 30, and an open-ended rebreathing bag 38 is shown connected to the port 32 via a length of tube 40, which provides the outlet tube with a suitable volume. However, a ventilation apparatus may well be connected to the port 32 provided that the port 30 is closed simultaneously, or the inlet of a carbon di-oxide absorber (not shown) may be connected to the port 32, the outlet of the absorber being connected to the port 30, thereby providing a closed circuit, circulating system.

In operation, during spontaneous respiration, fresh gases are inhaled by the patient through the inner tube 28 and the jet 20. Exhaled gases are directed through the jet 20 back into the inner tube 28. Most of the dead space gases followed by alveolar gases are preferentially directed into the inner tube 28 distending the bag 36, as in a modified Mapleson-'A' system, until the pressure increases sufficiently to cause the remainder of expired gases to pass through the space 23 into the outer tube 26.

When the apparatus is to be used in a controlled ventilation mode, the bag 36 is closed off by means of the closure member 34 or a suitable plug. Ventilation can then be commenced using the bag 38, or a closed-end rebreathing bag in conjunction with a semi-closed pop-off valve, or a suitable ventilator. During controlled ventilation the active volume of the outer tube 26 should not be less than the patient's tidal volume. If it is, then the tube 40 is utilised to increase the volume as required.

In addition to the above, the inner supply tube 28 may be extended to minimise dead-space, should those skilled in the art require this with children. This is effected by means of a tubular dead-space minimising member 44 which fits into the inner connector 22 and projects into the body member 14, with the jet 20 removed as shown in FIG. 2. The member 44 has a bore of about 7 mm diameter. Thus, should the apparatus be used with children below 20 kg, the jet 20 is removed and the dead-space minimising member 44 inserted. This results in fresh gases being supplied nearer the patient and minimising circuit dead-space.

With the above apparatus a lower resistance to flow during the second half of expiration is obtained, in comparison with a conventional Mapleson-'A' circuit. The peak resistance to expiration in the apparatus of the invention never exceeds that of the Mapleson-'A' circuit under conditions of normal respiratory effort and furthermore occurs during the first and middle phases of expiration. This results in more physiological breathing and a better elimination of expired gases.

With the apparatus of the invention it is possible to use larger diameter thin-walled tubes resulting in a surface area over which heat exchange takes place that is much larger than with any known co-axial systems and slower movement of gases, so that better heat exchange takes place.

Finally, a significant advantage of the present invention is the ease and convenience of changing from controlled to spontaneous respiration, and vice versa, and the ease of including a circle absorber. Also when changing over from the Mapleson-'A'-like system to a Mapleson-'D' or 'E' system, and vice versa, there is no necessity to flush out any of the tubes or bags.

I claim:

1. A fluid flow control device for an anesthesia system, comprising;
   (a) tubular connecting means having a proximal end adapted for connection to a patient and a distal end,
   (b) a tubular supply member having a distal end adapted for connection to a supply of inhalation fluid and a proximal end, means for securing the proximal end of said tubular supply member in spaced relationship to the distal end of said tubular connecting member,
   (c) a tubular outlet member having a proximal end, means connecting the proximal end of said tubular outlet member about said distal end of said tubular connecting means and said proximal end of said tubular supply member such that the space between the proximal end of said tubular supply member and the distal end of the tubular connecting member is in direct free fluid communication with said tubular outlet member, said tubular outlet member having a distal end communicating to atmosphere,
   (d) flow ducting means interposed between the distal end of said tubular connecting member and the proximal end of said tubular supply member, permitting flow of inhalation fluid from said tubular supply member to said tubular connecting means, said flow ducting member acting to direct exhalation fluid from said tubular connecting member directly into said tubular supply member and depending upon a predetermined pressure or volume of inhalation fluid in said tubular supply member into the tubular outlet member for venting to atmosphere, and said flow ducting means comprises a jet secured in a fluid tight manner to said tubular connecting means and having an exit end projecting into the proximal end of said tubular supply member and being radially spaced therefrom.

2. The device according to claim 1, wherein the tubular outlet member surrounds at least in part the distal end of said tubular connecting means and the proximal end of said tubular supply member.

3. The device according to claim 1, wherein at least the distal end of said tubular connecting means and the proximal end the tubular supply member are aligned along the same axis and the tubular outlet member is arrayed co-axial therewith.

4. The device according to claim 3, wherein the cross sectional area of the annulus formed by the co-axially aligned tubular supply member and tubular outlet member is less than the cross sectional area of the tubular supply member.

5. The device according to claim 1, wherein said jet is removably secured to said tubular connecting member.

6. The device according to claim 1, wherein said tubular connecting means forms a part of a face mask.

* * * * *